(12) United States Patent
Roche et al.

(10) Patent No.: US 8,494,805 B2
(45) Date of Patent: Jul. 23, 2013

(54) METHOD AND SYSTEM FOR ASSESSING ORTHOPEDIC ALIGNMENT USING TRACKING SENSORS

(75) Inventors: Martin Roche, Fort Lauderdale, FL (US); Jason McIntosh, Sugar Hill, FL (US); Marc Boillot, Plantation, FL (US); Carlos Gil, Hallandale Beach, FL (US)

(73) Assignee: Orthosensor, Sunrise, FL (US)

( * ) Notice: Subject to any disclaimer, the term of this patent is extended or adjusted under 35 U.S.C. 154(b) by 0 days.

(21) Appl. No.: 13/185,889

(22) Filed: Jul. 19, 2011

(65) Prior Publication Data

US 2012/0232834 A1 Sep. 13, 2012

Related U.S. Application Data

(63) Continuation-in-part of application No. 12/764,072, filed on Apr. 20, 2010, now Pat. No. 8,000,926, which is a continuation-in-part of application No. 11/562,404, filed on Nov. 21, 2006, now Pat. No. 7,725,288.

(60) Provisional application No. 60/740,151, filed on Nov. 28, 2005, provisional application No. 61/498,647, filed on Jun. 20, 2011.

(51) Int. Cl.
*G01B 17/00* (2006.01)

(52) U.S. Cl.
USPC .............. 702/159; 702/158; 600/424; 606/90

(58) Field of Classification Search
USPC ............................................ 702/66, 72, 159
See application file for complete search history.

(56) References Cited

U.S. PATENT DOCUMENTS

| | | | |
|---|---|---|---|
| 5,274,363 | A | 12/1993 | Koved |
| 6,090,114 | A | 7/2000 | Matsuno et al. |
| 6,130,663 | A | 10/2000 | Null |
| 6,137,427 | A | 10/2000 | Binstead |
| 6,313,825 | B1 | 11/2001 | Gilbert |
| 6,546,277 | B1 | 4/2003 | Franck et al. |
| 6,937,227 | B2 | 8/2005 | Qamhiyah |
| 7,078,911 | B2 | 7/2006 | Cehelnik |
| 7,081,884 | B2 | 7/2006 | Kong |
| 7,092,109 | B2 | 8/2006 | Satoh |
| 7,130,754 | B2 | 10/2006 | Satoh |
| 7,139,418 | B2 | 11/2006 | Abovitz et al. |
| 7,309,339 | B2 | 12/2007 | Cusick |
| 7,392,076 | B2 | 6/2008 | Moctezuma de La Barrera |
| 7,395,181 | B2 | 7/2008 | Foxlin |
| 7,477,926 | B2 | 1/2009 | McCombs |
| 7,559,931 | B2 | 7/2009 | Stone |
| 7,604,645 | B2 | 10/2009 | Barzell et al. |
| 7,636,595 | B2 | 12/2009 | Marquart |
| 7,657,298 | B2 | 2/2010 | Moctezuma de la Barrera et al. |
| 7,660,623 | B2 | 2/2010 | Hunter et al. |
| 7,681,448 | B1 | 3/2010 | Preston et al. |
| 7,685,861 | B2 | 3/2010 | Lynch et al. |

(Continued)

*Primary Examiner* — Mischita Henson

(57) ABSTRACT

A method for determining orthopedic alignment is provided. The method includes monitoring a first and second sequence of signals transmitted from the first device to a second device, estimating a location of the first device from sensory measurements of the signals at respective sensors on the second device, calculating a set of phase differences, weighting a difference of an expected location and estimated location of the first device with the set of phase differences to produce a relative displacement, and reporting a position of an orthopedic instrument coupled to the first device based on the relative displacement.

30 Claims, 9 Drawing Sheets

U.S. PATENT DOCUMENTS

| | | |
|---|---|---|
| 7,689,032 B2 | 3/2010 | Strassenburg-Kleciak |
| 7,771,436 B2 | 8/2010 | Moctezuma et al. |
| 7,824,328 B2 | 11/2010 | Gattani et al. |
| 2001/0011175 A1 | 8/2001 | Hunter et al. |
| 2003/0132913 A1 | 7/2003 | Issinski |
| 2004/0011365 A1* | 1/2004 | Govari et al. ............... 128/899 |
| 2004/0024309 A1 | 2/2004 | Ferre et al. |
| 2004/0236424 A1 | 11/2004 | Berez et al. |
| 2004/0254584 A1 | 12/2004 | Sarin et al. |
| 2006/0092022 A1 | 5/2006 | Cehelnik |
| 2006/0161871 A1 | 7/2006 | Hotelling |
| 2006/0164241 A1 | 7/2006 | Makela |
| 2006/0224429 A1 | 10/2006 | Mathew |
| 2006/0235420 A1 | 10/2006 | Irving |
| 2006/0256090 A1 | 11/2006 | Huppi |
| 2007/0127039 A1 | 6/2007 | Njolstad |
| 2007/0175489 A1 | 8/2007 | Moctezuma et al. |
| 2008/0269599 A1 | 10/2008 | Csavoy et al. |
| 2009/0318836 A1 | 12/2009 | Stone et al. |
| 2010/0063508 A1 | 3/2010 | Borja et al. |
| 2010/0069911 A1 | 3/2010 | Borja et al. |
| 2010/0076505 A1 | 3/2010 | Borja et al. |
| 2010/0137869 A1 | 6/2010 | Borja et al. |
| 2010/0160771 A1 | 6/2010 | Gielen et al. |
| 2010/0210939 A1 | 8/2010 | Hartmann et al. |

* cited by examiner

PROCESSOR 231
COMMUNICATIONS 232
USER INTERFACE 233
MEMORY 234
BATTERY 235
ATTACHMENT 236

350

METHOD AND SYSTEM FOR ASSESSING ORTHOPEDIC ALIGNMENT USING TRACKING SENSORS

CROSS-REFERENCE TO RELATED APPLICATION

This application is a Continuation-In-Part of U.S. patent application Ser. No. 12/764,072 filed on Apr. 20, 2010; that application a Continuation-In-Part of U.S. patent application Ser. No. 11/562,404 filed on Nov. 21, 2006 claiming the priority benefit of U.S. Provisional Patent Application No. 60/740,151 filed Nov. 28, 2005, the entire contents of which are hereby incorporated by reference. This application also claims the priority benefit of U.S. Provisional Patent Application No. 61/498,647 filed Jun. 20, 2011 the entire contents of which are hereby incorporated by reference

BACKGROUND

1. Field

The present embodiments of the invention generally relates to the field of motion sensing, and more particularly to tracking devices.

2. Introduction

Medical tracking systems that employ motion detection analysis may include video camera, electromagnetic components, infrared devices or other components. Such systems generally include sensors that convert a physical signal into an electronic signal. The sensor performs the task of capturing the signal and converting it to a suitable format for processing. A medical tracking and detection system can include an input device for interpreting the sensory information and identifying object position and orientation. As one example, during total knee replacement surgery bone cuts can be made with use of accurate tracking systems, and physical guides and jigs, and more recently, by way of and patient specific instruments. Such medical system and instrument advances can assist with bone cuts to result in proper alignment and balance.

DETAILED DESCRIPTION

Figure 1:
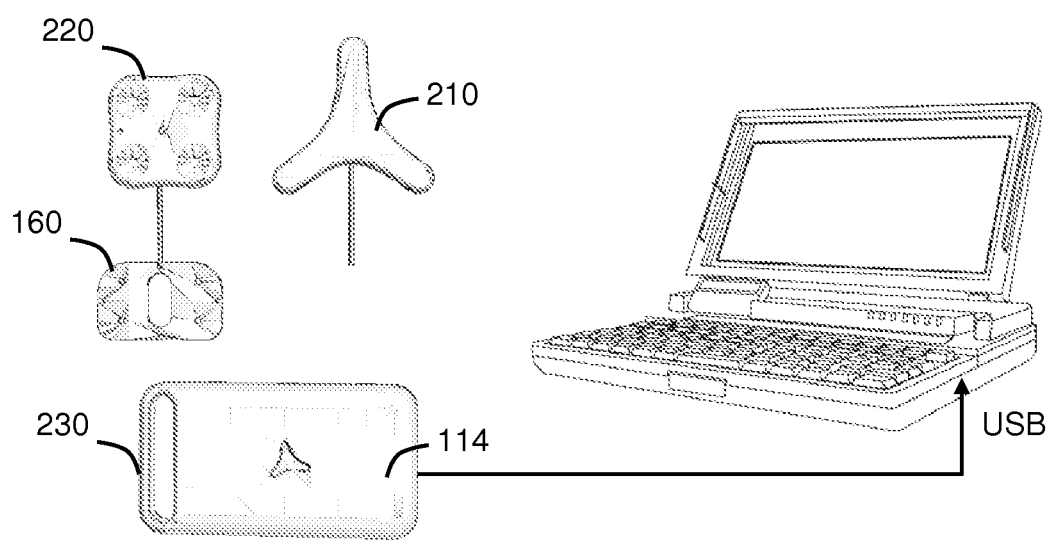
FIG. 1 illustrates an ultrasonic device for tracking object movement and position in accordance with an example embodiment.

While the specification concludes with claims defining the features of the invention that are regarded as novel, it is believed that the invention will be better understood from a consideration of the following description in conjunction with the drawing figures, in which like reference numerals are carried forward.

Broadly stated a system and method is provided for orthopedic instrumentation and tracking. The system can be coupled on or within orthopedic equipment, devices, tools, or prosthetic components. The system can provide position and location data in conjunction with parameter measurement of the muscular-skeletal system. Furthermore, the system disclosed can provide real-time user feedback configured for use in context of a surgical work-flow. As mentioned, the system provides quantitative measurements of muscular-skeletal system and prosthetic components to assess and support optimal installation. Examples of the navigation system adapted to a cutting jig and an insert is provided herein. The illustrations are examples in the broadest sense and the navigation methodology can be adapted to orthopedic tools in general and within the operating room for providing quantitative location and position data.

In one example, a tracking portion of the system provides bone cut visualization and range of motion analysis via one or more wand devices and a receiver device. The wand and receiver device can be attached to orthopedic equipment, devices, tools, or prosthetic components for position, alignment, and location thereof. In one embodiment, the components of the wand and receiver can be integrated within the orthopedic equipment, devices, tools, or prosthetic components. This reduces the number of components that the user uses, lowers user complexity, lowers cost through shared componentry, provides quantitative data to a procedure, and can reduce the time of the surgical procedure.

The wand is used to identify points of interest in three-dimensional space via a wand tip. The tracking system permits precise tracking and location sensing. The wand tip does not require any electronics or sensors. The wand can be affixed to an object to track its movement and orientation within proximity of the receiver. A measurement portion of the system includes sensors for measuring a parameter of the muscular-skeletal system. An example of parameter measurement is a force, pressure, or load measurement. In one embodiment, the sensors reside in a prosthetic component of an artificial joint system. The prosthetic component when installed provides quantitative measurement data that can be used to assess the installation of the joint. Sensory feedback and guidance provides audio and visual indication of work flow steps and the wand's location and orientation.

FIG. 1 depicts an exemplary embodiment of an orthopedic system 100 for assessing bone cuts, gap distances and alignment. The system 100 includes a receiver 220 with an attachment mechanism to a plate 160, a transmitter 210 that transmits sensory signals to the receiver 220; and a pod 230 communicatively coupled to the receiver 220 and the transmitter 210. The pod 230 interprets the sensory signals and determines a position and orientation of the transmitter 210 with respect to the receiver 220. This permits the system 100 to report cut angle information when the plate 160 is positioned onto an exposed bone cut. In one arrangement the pod 230 includes a local display 114 mounted thereon for displaying positional information such as the cut angle. The pod 230 can communicate the positional information to the remote device 104 through a communication port which can display the information on a Graphical User Interface (GUI) 108 in a detailed format. As one example, the port can be USB to provide data communication and low voltage power. The pod 230 is shown as a separate device although the internal electronics of the pod in other embodiments can be designed instead within the housing structure of the receiver 220.

FIG. 2 depicts exemplary components of the orthopedic system 100 in accordance with one embodiment. As illustrated the system 100 comprises the pod 230, the transmitter 210 and the receiver 220. Not all the components shown are required; fewer components can be used depending on required functionality. The pod 230 can couple to the transmitter 210 and the receiver 220 over a wired connection 251 as shown. In another configuration the transmitter 210 is wireless to the pod 230 and receiver 220 as will be explained ahead. In the configuration shown, the pod 230 contains the primary electronics for performing the sensory processing of the sensory devices. The transmitter 210 and the receiver 220 contain few components for operation, which permits the sensory devices to be low-cost and light weight when mounted. In another configuration, the primary electronic components of the pod 230 are miniaturized onto the receiver 220 with the battery 235; thus removing the pod and permitting a wireless system.

The Transmitter 210 receives control information from the pod 230 over the wired connection 251 for transmitting sensory signals. In one embodiment, the transmitter 210 comprises three ultrasonic transmitters 211-213 for each transmitting signals (e.g., ultrasonic) through the air in response to the received control information. Material coverings for the transmitters 211-21 are transparent to sound (e.g., ultrasound) and light (e.g., infrared) yet impervious to biological material such as water, blood or tissue. In one arrangement, a clear plastic membrane (or mesh) is stretched taught. The transmitter 210 may contain more or less than the number of components shown; certain component functionalities may be shared as integrated devices. Additional ultrasonic sensors can be included to provide an over-determined system for three-dimensional sensing. The ultrasonic sensors can be MEMS microphones, receivers, ultrasonic transmitters or combination thereof. As one example, each ultrasonic transducer can perform separate transmit and receive functions.

The transmitter 210 also includes a user interface 218 (e.g., button) that receives user input for requesting positional information. In one arrangement, a multi-state press button can communicate directives to control or complement the user interface. It can be ergonomically located near the finger area to permit single handed use. The transmitter 210 may further include a haptic module with the user interface 214. As an example, the haptic module may change (increase/decrease) vibration to signal improper or proper operation. With the wired connection 251, the transmitter 210 receives amplified line drive signal's from the pod 230 to drive the transducers 211-213. The line drive signals pulse or continuously drive the transducers 211-212 to emit ultrasonic waveforms. In a wireless transmitter 210 configuration, the electronic circuit (or controller) 214 generates the driver signals to the three ultrasonic transmitters 211-213 and the battery 215 provide energy for operation (e.g., amplification, illumination, timing, etc). The IR transmitter 216 sends an optical synchronization pulse coinciding with an ultrasonic pulse transmission when used in wireless mode; that is, without line 251. A battery 218 can be provided for the wireless configuration when the line 251 is not available to provide power of control information from the pod 230. The communications port 216 relays the user input to the pod 230, for example, when the button of the interface 214 is pressed.

The Receiver 220 includes a plurality of microphones 221-224, an amplifier 225 and a controller 226. The microphones capture ultrasonic signals transmitted by the transducers 211-213 of the transmitter 210. The amplifier 225 amplifies the captured ultrasonic signals to improve the signal to noise ratio and dynamic range. The controller 226 can include discrete logic and other electronic circuits for performing various operations, including, analog to digital conversion, sample and hold, and communication functions with the pod 230. The captured, amplified ultrasonic signals are conveyed over the wired connection 251 to the pod 230 for processing, filtering and analysis. A thermistor 227 measures ambient air temperature for assessing propagation characteristics of acoustic waves when used in conjunction with a transmitter 210 configured with ultrasonic sensors. An optional photo-diode 229 may be present for supporting wireless communication with the transmitter 210 as will be explained ahead. An accelerometer 227 may also be present for determining relative orientation and movement. The accelerometer 227 can identify 3 and 6 axis tilt during motion and while stationary.

An attachment mechanism 228 permits attachment to the plate 160 (see FIG. 1) and other detachable accessories. As one example, the mechanism can be a magnetic assembly with a fixed insert (e.g., square post head) to permit temporary detachment. As another example, it can be a magnetic ball and joint socket with latched increments. As yet another example, it can be a screw post o pin to a screw. Other embodiments may permit sliding, translation, rotation, angling and lock-in attachment and release, and coupling to standard jigs or plates by way of existing notches, ridges or holes.

The Pod 230 comprises a processor 233, a communications unit 232, a user interface 233, a memory 234 and a battery 235. The processor 231 controls overall operation and communication between the transmitter 210 and the receiver 220, including digital signal processing of digital signals, communication control, synchronization, user interface functionality, temperature sensing, optical communication, power management, optimization algorithms, and other processor functions. The processor 231 supports transmitting of timing information including line drive signals to the transmitter 210, receiving of captured ultrasonic signals from the receiver 220, and signal processing for determination of positional information related to the orientation of the transmitter 210 to the receiver 220 for assessing and reporting cut angle information.

The processor 233 can utilize computing technologies such as a microprocessor (uP) and/or digital signal processor (DSP) with associated storage memory 108 such a Flash, ROM, RAM, SRAM, DRAM or other like technologies for controlling operations of the aforementioned components of the terminal device. The instructions may also reside, completely or at least partially, within other memory, and/or a processor during execution thereof by another processor or computer system.

The electronic circuitry of the processor 231 (or controller) can comprise one or more Application Specific Integrated Circuit (ASIC) chips or Field Programmable Gate Arrays (FPGAs), for example, specific to a core signal processing algorithm or control logic. The processor can be an embedded platform running one or more modules of an operating system (OS). In one arrangement, the storage memory 234 may store one or more sets of instructions (e.g., software) embodying any one or more of the methodologies or functions described herein.

The communications unit 232 can further include a transceiver that can support singly or in combination any number of wireless access technologies including without limitation Bluetooth, Wireless Fidelity (WiFi), ZigBee and/or other short or long range radio frequency communication protocols. This provides for wireless communication to a remote device 104 (see FIG. 1). An Input/Output port within the communications unit 232 permits portable exchange of information or data, for example, by way of Universal Serial Bus (USB).

The memory 234 stores received ultrasonic waveforms and processing output related to tracking of received ultrasonic waveforms and other timing information, state logic, power management operation and scheduling. The battery 235 powers the processor 231 and associated electronics thereon and also the transmitter 210 and the receiver 220 in the wired configuration.

The user interface 233 can include one or more buttons to permit handheld operation and use (e.g., on/off/reset button) and illumination elements 237 to provide visual feedback.

In a first arrangement, the receiver 220 is wired via a tethered electrical connection 251 to the transmitter 210. Timing information from the pod 230 tells the transmitter 210 when to transmit, and includes optional parameters that can be applied to pulse shaping. The processor 231 on the pod 230 establishes Time of Flight measurements according to the timing with respect to a reference time base in the case of ultrasonic signaling. In a second arrangement, the receiver 220 is wirelessly coupled to the transmitter 210 via an optical signaling connection. The infrared transmitter 216 on the transmitter 210 transmits an infrared timing signal with each transmitted pulse shaped signal. The infrared timing signal is synchronized with the transmitting of the ultrasonic signals to the receiver 220. The receiver 220 can include the photo diode 229 which the pod 230 monitors to determine when the infrared timing signal is received. The pod 230 employs this infrared timing information to establish Time of Flight measurements with respect to a reference transmit time. The infrared transmitter and photo diode establish transmit-receive timing information to within microsecond accuracy.

For a single transmitter operation, the Receiver 220 senses ultrasonic waves transmitted by the Transmitter 210. The Receiver 220 determines positional information of the transmitter 210 from range and localization of received ultrasonic waves captured at the microphones. Notably, one or more transmitters 210 can be present for determining orientation among a group of transmitters 210. The pod 230 wirelessly transmits this information as positional data (i.e., translation vectors and rotational matrices) to the Display Unit 104. The Display Unit 104 processes the positional data to provide 3D visual rendering of alignment and orientation angles of the Transmitter 210 (and any devices thereto mounted, such as the plate 160). The Transmitter 210 intermittently transmits ultrasonic waves by way of the three (3) Transmitters. The transmission cycle varies over a 5-10 ms interval at each of the three transmitters; each transmitter takes turns transmitting an ultrasonic waveform. The ultrasonic waveforms propagate through the air and are sensed by the microphones on the Receiver 220. The Receiver 220 determines positional information of the Wand from range and localization of transmitted ultrasonic waveforms. The Receiver 220 measures the position and orientation of the Wand(s) in three-dimensions (3D) with respect to the Receiver 220 coordinate system.

Figure 2A:
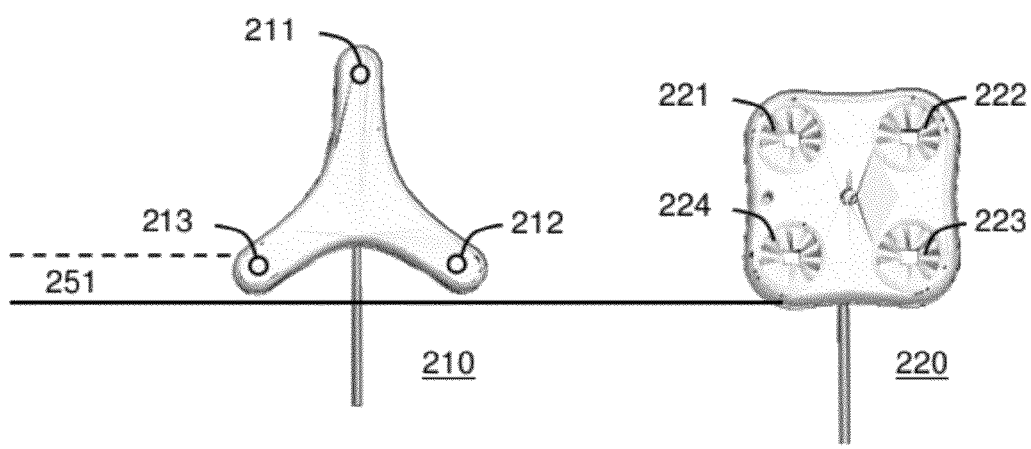
FIG. 2A illustrates an ultrasonic transmit device for beaconing an orientation and position in accordance with an example embodiment.
Figure 2B:
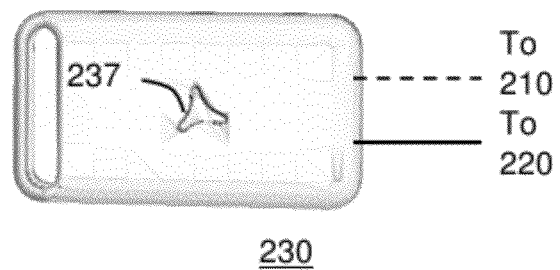
FIG. 2B illustrates an ultrasonic receive device for locating a beaconing ultrasonic device in accordance with an example embodiment.
Figure 3A:
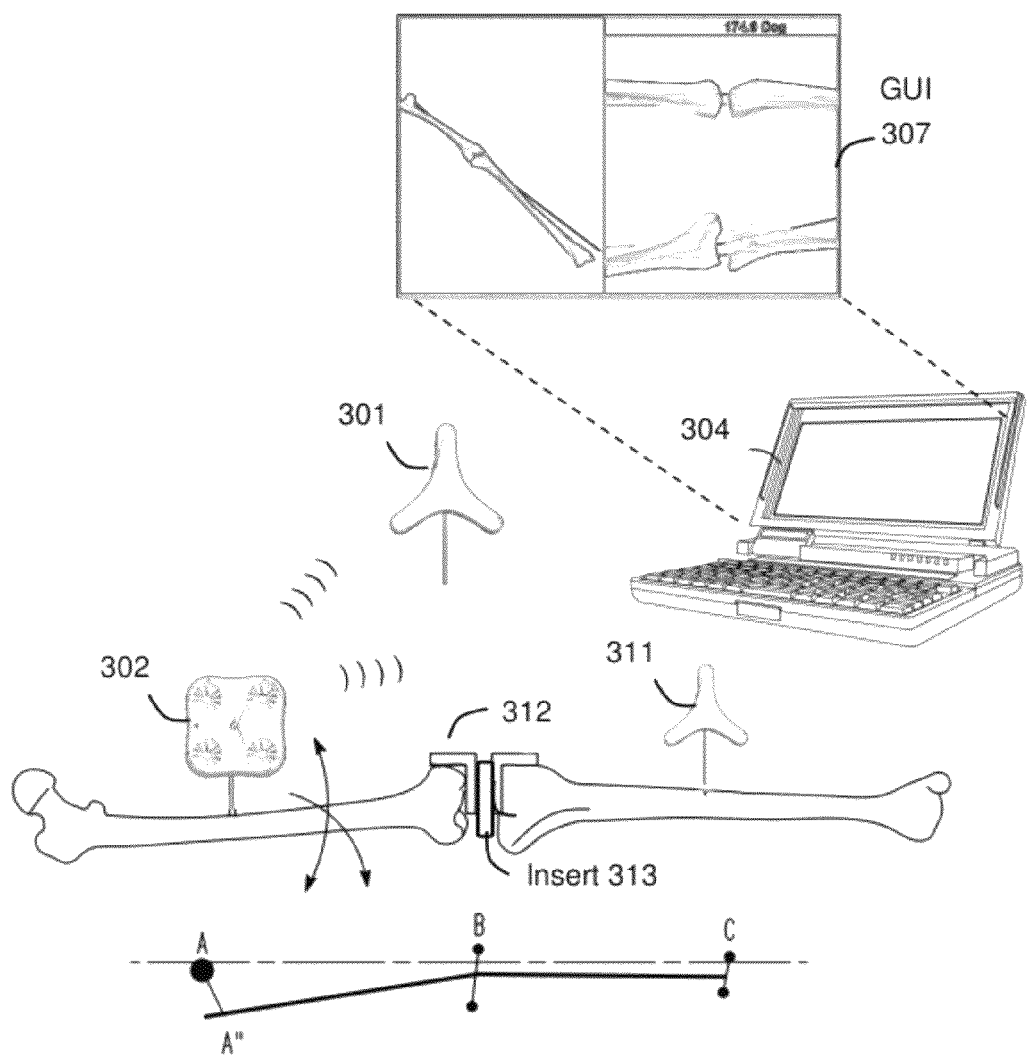
FIG. 3A illustrates an exemplary ultrasonic system for reporting pointing location and alignment in an example embodiment.

FIG. 3A illustrates a system 300 suitable for use as a positional measurement and alignment tool for orthopedic applications in accordance with an example embodiment. System 300 is shown in an intra-operative setting to assess an alignment of the femur and tibia bones. The system 300 includes the first device 301 (also 210 FIG. 2, hereinafter wand) and the second device 302 (also 220, hereinafter receiver). The wand 301 and receiver 302 are low cost disposable components delivered in a sterilized package. The receiver 302 can communicate with the remote system 304 to report wand tip location, positional information and an orientation of the wand 301 in real-time. The wand 301 and the receiver 302 communicate directly with one another without outside reliance on a supervisory system; that is, the receiver 302 can determine the location and orientation of the wand 301 within local view and with respect to its own coordinate system.

The wand 301 is used to register points of interest in three-dimensional space with respect to the receiver 302; points of interest can be spatial locations, for example, anatomical or structural locations on a bone or structure 312. The wand 301 can also measure and report distance (e.g., mm, cm) between registered spatial points, for example, a gap distance between the distal femur and proximal tibia to determine a suitable sized insert 313, or trial insert. It can also be used to identify displacement, for example, an edge point or perimeter trace of an insert relative to its projected insertion location. The wand 301 can also thereafter be affixed at these locations to report rotations and translations of the underlying object (e.g., bone, jig, insert, prosthetic etc) at these points, for example, relative to a reference orientation. This also permits for full range tracking and reporting of kinematic behavior. Such information can be used during the surgery to report range of joint motion and for comparison of post-surgical results.

In one embodiment, the system 300 comprises the receiver 302 coupled to the jig 312, and the wand 301 to register points of interest on a first and second bone with respect to the jig 312. The receiver 302 and wand 301 employ ultrasonic sensing and tracking to determine wand 302 orientation and location relative to receiver 302 and the jig 312. Based on the registered points of interest, the receiver 302 assesses and reports parameters related to the orientation of the jig 312 for aligning the first and second bone. The wand tip locations and orientations can also be stored for reference on the receiver 302. Similarly, the system 300 can report alignment of the bones or jigs 312 by way of the wand 301 and the receiver 302 from these points of interest. The system 300 can assist in assessing alignment of the jigs 312 and bones for example, in knee replacement procedures. Software configurable parameters permit operation beyond the 3.0 meter application range shown.

In one example, alignment is achieved when the points of the femur head (A'), knee center (B') and ankle (C') are positioned in a straight line as indicated by a positioning location of the tip of wand 301 at the second locations at separate times. Femur head identification of point (A') can be determined by affixing receiver 302 to the distal end of the femur and placing wand 301 at a stationary location in view (e.g., 1 m distance from receiver 302). The femur is then rotated in a pattern for approximately 10-15 seconds to resolve the spherical center (femur head) as described in Provisional Patent Application No. 61/291,725 while the hip is sufficiently still. Upon establishing point (A'), the wand tip is then used to register the knee center (e.g., distal femur center) point B' when the leg is in flexion. Other anatomical locations can be registered for providing further alignment information, for example, the proximal tibia. Thereafter, the wand tip is used to register the medial alveolus and the lateral alveolus which establishes the ankle center C' (e.g., center=0.6*medial<x,y,z>)+0.4*lateral<x,y,z>).

Once these three (or more) points A', B' and C' are registered, wand 301 can be affixed midway on the tibia and in view of receiver 302. This permits real-time tracking of the tibia relative to the femur bone when the leg is in extension (straight) or in flexion (bent). In this fixed relationship, the receiver 302 can track a position and orientation of wand 301 relative the receiver's own coordinate system which inherently reveals any rotations and translations of the tibia relative to the femur (e.g., axial twist, left-right, up-down, forward-backward, and combinations thereof). As noted previously, this permits the system 300 to track and report a range of motion and associated kinematic information (e.g., axial twist, rotations, alignment) in accordance with a patient's expected orthopedic behavior during the procedure.

Certain aspects of alignment preparation can be performed before hand; for example, calibrating the receiver 302 to jig 312 or wand 301. It can also transmit the positional information to associated wireless devices (e.g., laptop, cell phone, net book) like the remote system 304 and upload the information to a server on a network for example one connected to electronic medical or health care records. The system 300 can assess and report in real-time the position of these points for determining alignment, or other registered points, by way of a graphical user interface on the communication device 304.

In a first embodiment, the 300 comprises the ultrasonic transmitter 301 on a first device for transmitting at a first location a first sequence of ultrasonic signals through air, the receiver 302 on a second device for capturing the first sequence of ultrasonic signals and a second sequence of ultrasonic signals transmitted by the ultrasonic transmitter on the first device during movement to a second location, a phase detector (software operating in processor 231, see FIG. 2) on the second device operatively coupled to the receiver for identifying a series of phase differences between the first sequence of ultrasonic signals and the second sequence of ultrasonic signals, and the processor (processor 231, see FIG. 2) on the second device operatively coupled to the phase detector and a sensing unit comprising the receiver for updating an expected location of the first device using the series of phase differences. The processor measures a first series of Time of Flights (TOF) between the transmitting of the first sequence of ultrasonic signals and the capturing of the second sequence of ultrasonic signals, and producing therefrom the expected location of the first device at the first location, measures a second series of Time of Flights (TOF) between the transmitting of the first sequence of ultrasonic signals and the capturing of the second sequence of ultrasonic signals, and producing therefrom an estimated location of the first device at the second location, determines a relative displacement of the first device by weighting a difference of the expected location and estimated location with the phase difference, and reports a position of an orthopedic device coupled to the first device in accordance with the relative displacement, wherein the estimated location is determined from the second series of Time of Flight (TOF) measurements, and the relative displacement is evaluated within a minimized error region determined from a series of differential time of flight (dTOF) measurements.

As illustrated, a third device 311 can transmit ultrasonic signals to the second device 302 for reporting a position and orientation of the third device 311 relative to the second device 302, where the second device is attached to a first bone (e.g., femur) and the third device is attached to a second bone (e.g., tibia) for communicating there between during range of motion. Notably, the devices can be interchanged in location on the bones, for instance, receiver 302 is on tibia, and wand 311 is on femur. In this configuration, the receiver 302 may expose microphones on both a front and back side for permitting the wand 301 to mark points on either side of the tibia, for example, the proximal and the distal ends. 3. The third device 311 permits for tracking of the tibia during movement with respect to the femur. The tibia can thus be moved to a suitable location when using the wand 301 to register points, for example, keeping the leg straight when registering ankle points, or keeping the leg bent at the knee when registering proximal tibia plateau points. The orthopedic device can be a cutting jig, a prosthetic component, or a trial insert. Examples of these orthopedic devices are described in U.S. patent application Ser. No. 12/900,662 entitled "Navigation Device Providing Sensory Feedback" filed Oct. 8, 2010 and U.S. patent application Ser. No. 12/900,878 filed Oct. 8, 2010 entitled "Navigation System and User Interface For Directing a Control Action", the entire contents of which are hereby incorporated by reference.

Figure 3B:
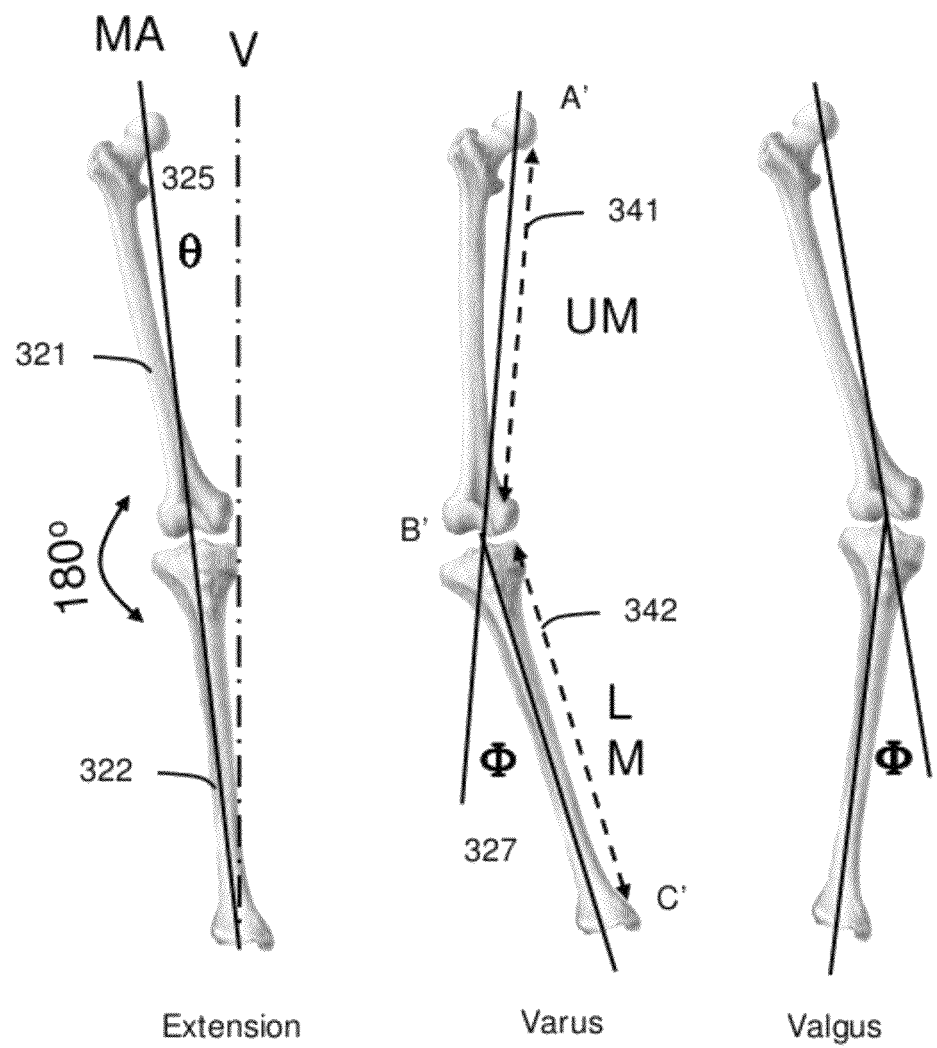
FIG. 3B illustrates anatomical deviations with respect to mechanical axis alignment in accordance with an example embodiment.

FIG. 3B illustrates alignment along a mechanical axis of a leg for normal and abnormal conditions in accordance with an example embodiment. In extension, the femur 321 and tibia 322 of the leg are aligned along the mechanical axis (MA). The MA is approximately 0~=6 degrees 325 from the vertical (V) at the ankle; and approximately 15-18 degrees from the vertical (V) at the knee (Q-angle) for a straight leg in standing position. As illustrated in the center subplot, a varus deformity is an outward angulation of the distal segment of a bone or joint with an alignment angle (or error) described by $-\Phi 327$. As illustrated in the right subplot a valgus deformity is a term for the inward angulation of the distal segment of a bone or joint with an alignment angle (or error) described by $+\Phi 327$.

The system 300 reports the alignment angle $\Phi 327$ between the first line 341 and the second line 342 as part of the positional location (information). The first line 341 is defined by the first point A' at a first time and a second point B' at a second time. The second line 342 is defined by the pointing location of the wand 301 at the second point B' and a third point C' at a third time. The pointing locations as determined by the pulse shaped signals are stored in the history for reference. The system 300 can include multiple points for determining alignment and is not limited to a 3-point profile.

As previously indicated the receiver 302 itself can display alignment information or report the information to remote system to provide visualization. As one example, the LED lights 224 on the receiver 302 illuminate in accordance with a detected alignment. A single multi-color LED will turn green for perfect alignment (0°), turn yellow if less than 2°, and turn red if alignment is off by 3° or more. With single color LEDS, a varus condition will illuminate the corresponding medial (inside) LED, a valgus condition will illuminate the corresponding lateral (outside) LED, and an alignment less than 1° will show all LEDS green. Other illumination patterns are herein contemplated and are not limited to those described. Similarly, the GUI 304 can report alignment information via text representation of the alignment error or by color coding displayed line segments.

Figure 3C:
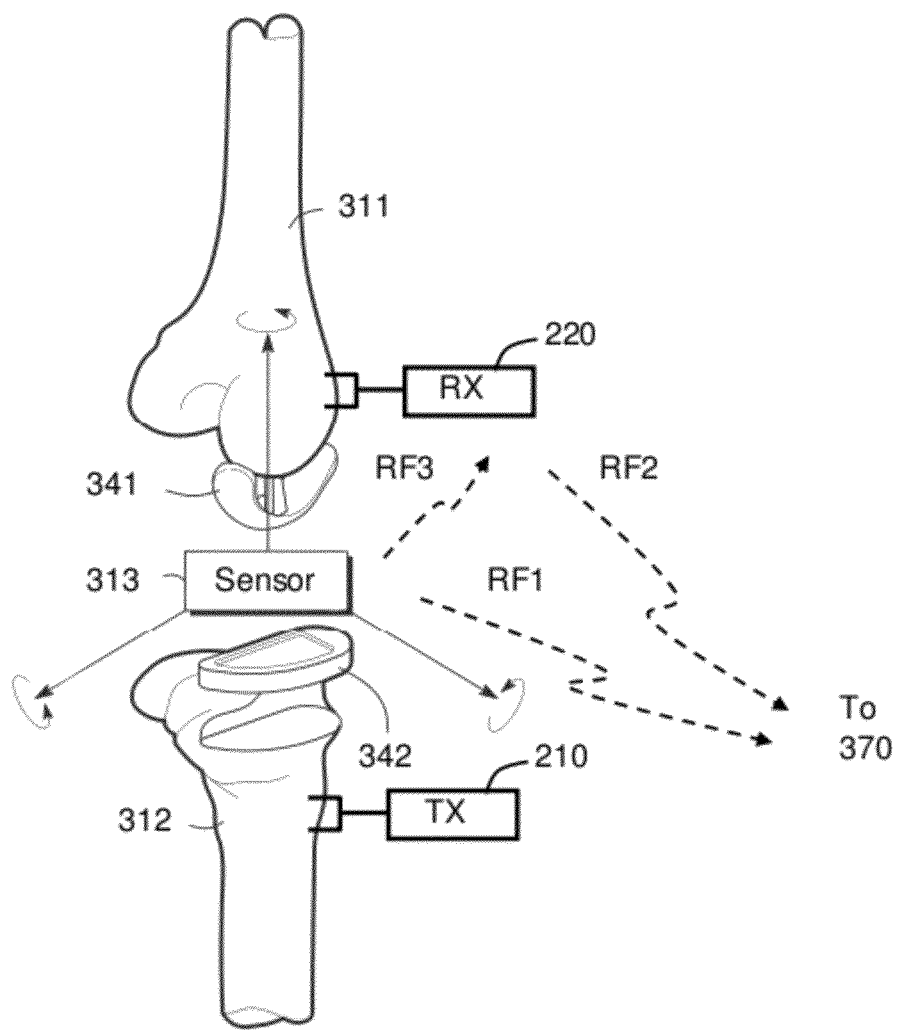
FIG. 3C pictorially illustrates a knee with sensorized components in accordance with one embodiment.
Figure 3D:
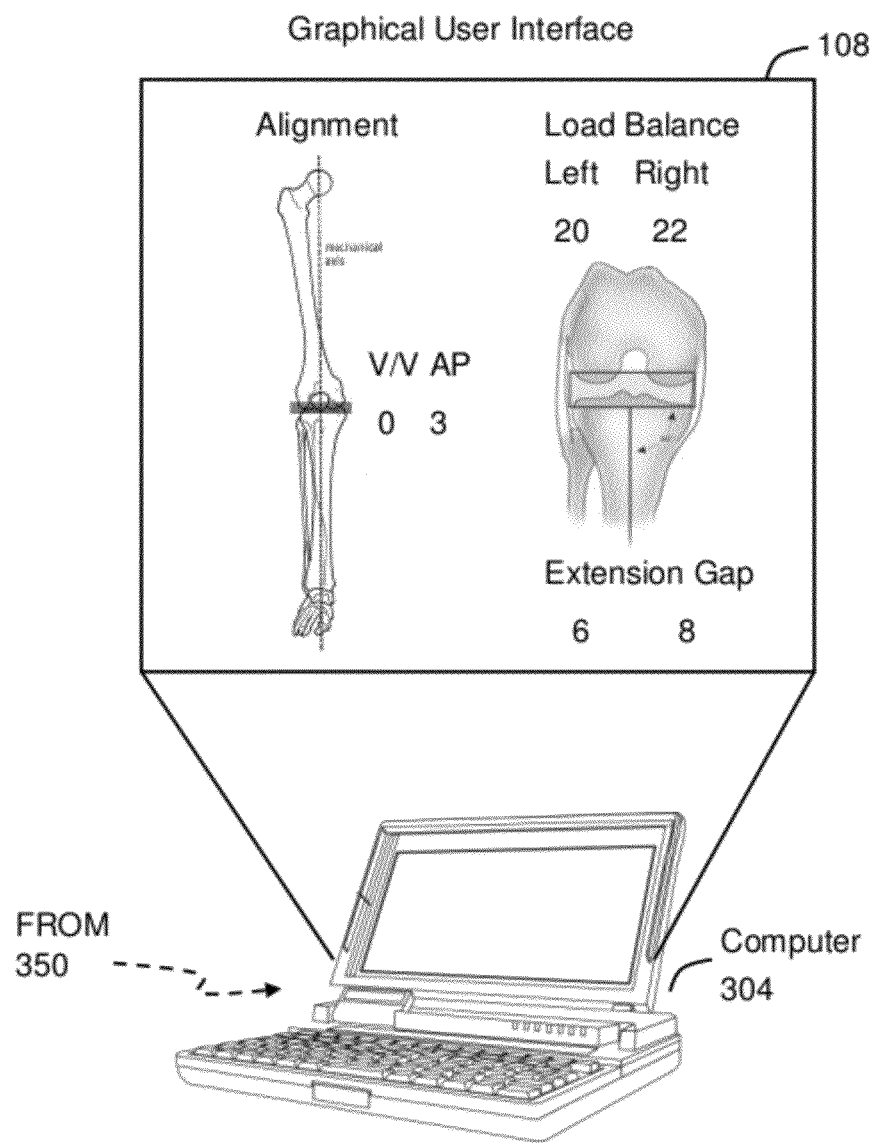
FIG. 3D illustrates an orthopedic alignment and balance GUI in accordance with one embodiment.

FIGS. 3C and 3D together illustrate one implementation of an orthopedic alignment and balance system for total knee replacement procedures. It employs the aforementioned tracking components and the visualization GUI 108. As shown, the Receiver (RX) 220 is mounted onto the femur 311 above the femur prosthetic 341 component, the Wand (TX) 210 is mounted on the tibia 312 below the tibia tray prosthetic 342 component, and the load sensor 302 is inserted between the femur prosthetic 341 and the tibia prosthetic 342. There are various communication path configurations (e.g., RF1, RF2 and RF3) for establishing integrated communication between the load sensor 301, the RX 220 and the computer 104 exposing the Graphical User Interface (GUI) 108. The system 300 tracks alignment and balance during range of motion and reports gap distance measurements. Extension gap and angles are reported on the GUI 108 during the tracking with prosthetic trials with a kinematic analysis associated with the inserted prosthetic trials and corresponding bone cut, permitting assessment of, trial insert sizing, and overall prosthetic fit. One exemplary method of wireless parameter sensing and reporting by way of a trial insert sensor is disclosed in U.S. patent application Ser. No. 12/825,724 filed Jun. 29, 2010 the entire contents of which are hereby incorporated by reference In yet other arrangements, the load sensing unit 170 can include piezoelectric, capacitive, optical or temperature sensors or transducers to measure the compression or displacement. It is not limited to ultrasonic transducers and waveguides. One exemplary method of force sensing is disclosed in U.S. patent application Ser. No. 12/826,329 filed Jun. 29, 2010 the entire contents of which are hereby incorporated by reference.

Figure 4:
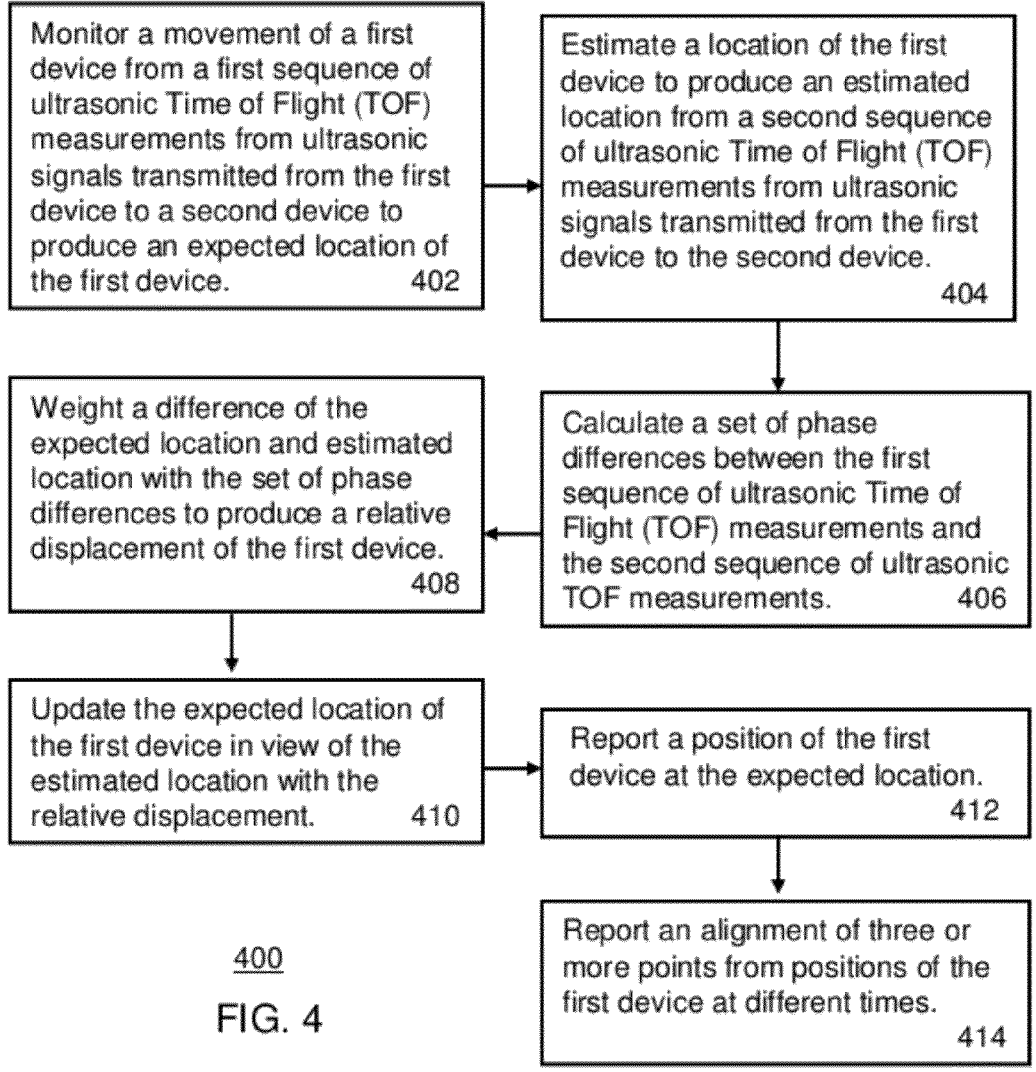
FIG. 4 illustrates steps resolving movement and position using ultrasonic sensing in accordance with an example embodiment.

Referring to FIG. 4, a method 400 for positional measurement is shown in accordance with an example embodiment. When describing the method 400, reference will be made to FIGS. 2A, 2B, 3A, 3B and 3C although the method 400 can be practiced in any other suitable system or device. Moreover, the steps of the method 400 are not limited to the particular order in which they are presented in FIG. 4. The inventive method can also have a greater number of steps or a fewer number of steps than those shown in FIG. 3.

At step 402, the second device 220 (e.g., receiver 302) monitors a movement of the first device 220 (e.g., wand 301) by measuring a first sequence of Time of Flight (TOF) measurements from ultrasonic signals transmitted from the first device 220 to the second device 220. The measurements produce an expected location of the first device 220. The expected location is a location that is expected in view of the TOF measurements.

Three (3) or more transmitters on the first device 220 perform a sequence of transmissions that occur simultaneously, staggered in time (e.g., delayed transmit) or combination thereof. Each transmitter can transmit at a same frequency (e.g., 40 KHz) and at different frequencies (e.g., 40, 64, 80, 120 KHz). Different fundamental frequency transmit timing patterns can be based on predetermined interference patterns—due to constructive and deconstructive interference of the ultrasonic energy waves. Accordingly, the transmit duration (amount of time the transmitter is vibrating) can be set as a function of the frequencies and timing sequence. Given the speed of sound at 343 m/s, the TOF measurement establishes the distance from each transmitter on the first device 220 to the corresponding receiver on the second device 220 during the movement.

With regard to the components of FIG. 2A, the transmitter 201 receives from the controller 214 a driver signal that describes the transmit shape to be transmitted. As one example the shape can be a square wave that causes a transducer of the transmitter 201 to resonate. In another arrangement, the driver signal can be a frequency modulated or amplitude modulated driver signal provided by the controller 214. One example of pulse shaping is taught in U.S. Pat. No. 7,414,705 entitled "Method and System for Range Measurement" the entire contents of which are hereby incorporated by reference. Alternatively, timing information provided to the controller 214 from the receiver 302 can include pulse shape information or pulse shape parameters in real-time; that is, the second device 220 directs the first device 220 to transmit ultrasonic pulse signals with a specified shape and at a specified time. The shaping comprises generating an amplitude modulated region, frequency modulated region, constant frequency region, phase modulated region, a chirp region, or a combination thereof Returning back to FIG. 4, at step 404, the receiver 220 estimates a location of the first device 220 to produce an estimated location from a second sequence of ultrasonic Time of Flight (TOF) measurements from ultrasonic signals transmitted from the first device to the second device. The estimated location is a point in three-dimensional (3D) space (e.g., <x,y,z>); it can be determined when there is no movement of the first device 220. The second sequence corresponds to simultaneous or staggered-in-time ultrasonic transmissions. The first device 220 can modify (adjust) the sequence pattern as a function of the movement detected by the accelerometer, for example, when it is accelerating, decelerating or when it is held still. The time of flight is a round trip time, that accounting for processing delays, is calculated between when an ultrasonic signal is transmitted from the first device 220 to when it is received (arrives) at the second device 220. Threshold and logic gates in hardware and software can determine when it is received (detected).

One example of detecting arrival time is taught in U.S. patent application Ser. No. 11/562,404 entitled "Method and System for Object Control" the entire contents of which are hereby incorporated by reference. This can include calculating a first Time of Flight of a first pulse shaped signal emitted at a first time from a first transmitter on the first device and received on a first microphone on the second device, calculating a second Time of Flight of a first pulse shaped signal emitted at a second time from a second transmitter on the first device and received on a second microphone on the second device, and calculating a third Time of Flight of a first pulse shaped signal emitted at a third time from a third transmitter on the first device and received on a third microphone on the second device. That is, a time of flight is calculated at each microphone based on the transmitting of only one ultrasonic pulse shaped waveform. For instance, Tx 201 transmits and Rx 221-223 all determine a corresponding TOF; then, Tx 202 transmits and all Rxs listen, and so on.

In a first arrangement, the second device 220 is wired via a tethered electrical connection (e.g., wire) to the first device 220. That is, the communications port of the first device 220 is physically wired to the communications interface of the second device 220 for receiving timing information. The timing information from the second device 220 tells the first device 220 when to transmit and includes optional parameters that can be applied to the ultrasonic signal for pulse shaping. The processor on the second device 220 employs this timing information to establish the first, second and third Time of Flight measurements with respect to a reference time base.

In a second arrangement, the second device 220 is communicatively coupled to the first device 220 via a wireless signaling connection. As previously indicated an infrared transmitter on the first device 220 can transmit an infrared timing signal with each transmitted pulse shaped signal. The receiver 302 can include a photo diode for determining when the infrared timing signal is received. In this case the communications port of the first device 220 is wirelessly coupled to the communications interface of the second device 220 by way of the infrared transmitter and the photo diode for relaying the timing information to within 3 microsecond accuracy (~1 mm resolution). The processor 233 on the second device 220 employs this infrared timing information to establish the first, second and third Time of Flight measurements with respect to a reference transmit time.

At step 406, the receiver 220 calculates a set of phase differences between the first sequence of ultrasonic Time of Flight (TOF) measurements and the second sequence of ultrasonic Time of Flight (TOF) measurements. A phase difference for each transmit-receiver pair is calculated for the set of phase differences. Phase differences are illustrated and discussed in FIG. 9 of the parent patent application. As one example, there are three phase differences for the ultrasonic signals sent from the transmitters 201-203 of the first device 220 to the receivers 221-223 of the second device 220. The phase difference is a time difference between a first received ultrasonic signal and a second received ultrasonic signal at the same transmitter with respect to a phase of the first received ultrasonic signal.

One example of detecting phase differences is taught in U.S. patent application Ser. No. 11/146,445 the entire contents of which are hereby incorporated by reference. The method step of detecting phase differences can further include calculating a first phase differential between a first transmitted ultrasonic signal and a previously received ultrasonic signal both captured at the first microphone, calculating a second phase differential between the first ultrasonic signal and a previously received ultrasonic signal both captured at the second microphone; and calculating a third phase differential between the first ultrasonic signal and a previously received ultrasonic signal both captured at the third microphone. That is a differential time of flight is calculated for each microphone based on the transmitting of a first ultrasonic waveform and a previously received ultrasonic waveform each at the respective microphone stored in the history.

Figure 5:
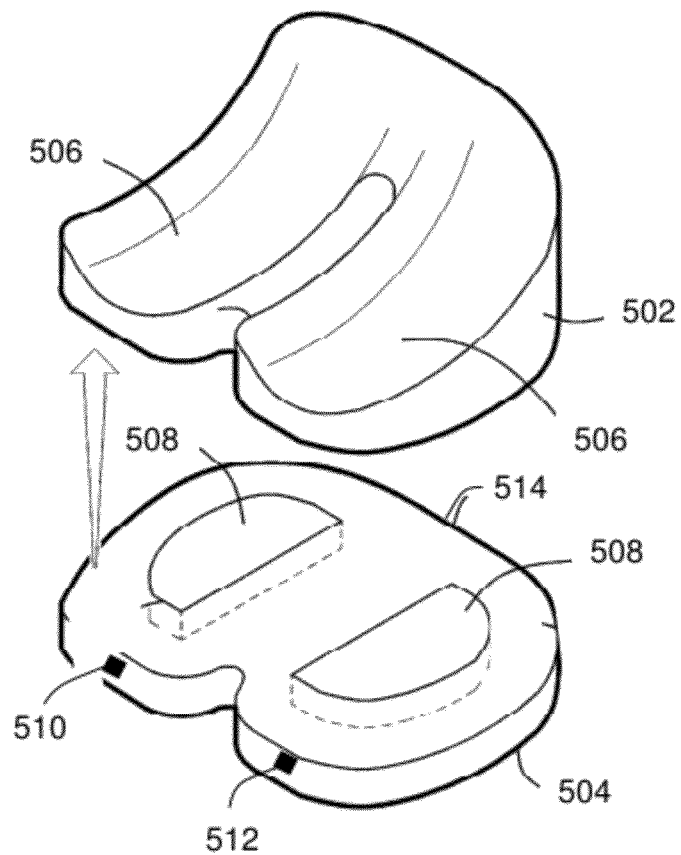
FIG. 5 illustrates a prosthetic component 500 in accordance with an example embodiment.

At step 408, the receiver 220 weights a difference of the expected location and estimated location with the set of phase differences to produce a relative displacement of the first device. One example of applying weighted differences is taught in U.S. patent application Ser. No. 11/562,404 the entire contents of which are hereby incorporated by reference (parent to the immediate application). FIG. 5 of that application illustrates an expected location, an estimated location, and a relative displacement of a first device 220 as determined by a second device 220.

The second device 220 determines the location and movement of the first device 220. In order to track its movement, a history of the first device 220 locations can be stored in the trajectory 430. The trajectory 430 can be a history of expected locations captured over time. An expected location is a weighted average of historic estimated locations that are smoothed over time. The estimated location 436 is a location determined from a direct analysis of the received ultrasonic signals. The trajectory 430 is generally smooth to reflect the continuous movement of the first device 220 relative to the second device 220.

While the first device 220 is moving, it can be expected that its motion will not dramatically depart from the trajectory 430. The object generally moves along a continuum of points. An expected location 432 of the first device 220 can fall within a variance determined from historic locations of the trajectory 430. Accordingly, a next location 432 of the first device 220 can be anticipated to fall within the expected location 432. The next location is also considered the estimated location 436 of the first device 220. The estimated location 436 is a measured position of a current first device 220 location from an analysis of received ultrasonic signals. The estimated 436 location may be accurate or inaccurate.

At step 410, the receiver 220 updates the expected location of the first device with the relative displacement in view of the estimated location. Briefly referring back to FIG. 5 of the parent application Ser. No. 11/562,404 the processor 233 keeps a history of estimated locations 436 and evaluates the history to determine if the estimated location 436 is close to the expected location 432. The relative displacement 438 can be updated based on how close the estimated location 436 is to the expected location 432. In such regard, the first device 220 can be tracked relative to the second device 220 based on relative displacements 438 alone. However, if the relative displacements 438 are imprecise, then over time, the expected location 432 may not match an actual location of the object. That is, the expected location 432 may not coincide with the actual, or absolute, location if the expected location is always updated only on relative displacements 438. Accordingly, the relative displacements 438 are updated to take into account an absolute position of the object by weighting the estimated location 436. However, only an estimate of the absolute position is provided; that is, the estimated location 436.

A phase difference 434 is calculated for the estimated location 436. The phase difference reveals a distance the first device 220 has moved. Accordingly, if the phase difference 434 combined with the estimated location places the first device 220 location outside of the expected location 432, then it can be determined that the estimated location 436 is incorrect. The relative displacement can then be updated based on the expected location 432 alone. If the phase difference combined with the estimated location as determined by the second device 220 places the first device 220 location inside the expected location 432, then it can be determined that the estimated location 436 is correct. The relative displacement can then be updated based on the estimated location 436 and the expected location 432. A weighting can be applied to soft limit the relative displacement updated instead of applying the hard limit. In such regard, the relative displacement can be updated based on a weighting of the estimated location and the expected location.

At step 412, the receiver 220 reports a position of the first device 220 at the expected location. The actual location of the first device 220 is identified by the tip 207, see FIG. 2A. The position of the first device 220 can also describe its orientation. The pointing location of the first device 220 can thus represent the orientation with respect to tip 207 position. To resolve the position, referring to FIG. 2A, the second device 220 converts the time of flight and set of phase difference measurements calculated from each of the received ultrasonic signals at the three microphones 221-223 to three spatial points, and transforms the three spatial points to X, Y and Z rotations around the tip 207. This establishes the orientation of the first device 220. The second device 220 determines the rotations with respect to its local coordinate system (at the origin). The second device 220 thereafter applies a series of translations and rotations to map the first device's 200 coordinate system to its own local coordinate system. This transformation establishes an orientation of the first device 220 and positional location of the tip relative to the second device 220. The mapping includes i) the first device 220 dimensions (e.g., 10×3×10 cm <w,l,h>) and component layout for the local coordinates of the transmitters and the tip 207 that are predetermined, and ii) the second device 220 dimensions (e.g., 6×2×8 cm, <w,l,h>) and component layout for the local coordinates of the microphones and its coordinate origin that are predetermined.

The positional location is where the tip 207 is located in three-dimensional space with respect to an orientation of the first device 220. The positional location can be represented in Cartesian coordinates or polar coordinates. It can be the same point in three-dimensional space even though the wand orientation (e.g., tilt, rotation). The positional location identifies the tip 207 location relative to the second receiver 220 and the spatial coordinates of the three or more transmitters 201-203 relative to the coordinate system of the second receiver 220. It can be reported via sensory feedback, graphical or text display and/or audibly. One example of sensory feedback via ultrasonic sensing and its principles of operation is taught in U.S. patent application Ser. No. 11/562,413 entitled "Method and System for Sensory Feedback" the entire contents of which are hereby incorporated by reference.

At step 412, the receiver 220 reports an alignment of three or more points from positions of the first device at different times. For example, as shown in FIG. 3A, the positional information (e.g., location of the wand tip, orientation) and the alignment can be further rendered to a 3D representation; for example, alignment of the femur and tibia based on resolving the hip center (e.g., femur head location) as previously described and touching the tip 207 of the first device 220 to two more anatomical locations (knee center and ankle center). The GUI 307 displays real-time updates to permit the user to visualize and assess multiple-point alignment. In the example shown, alignment is reported for varus and valgus deviations in accordance with the wand tip positional locations as shown in FIG. 3B.

FIG. 5 illustrates a prosthetic component 500 in accordance with an example embodiment. A cutaway view of prosthetic component 500 shows modules 508 that are housed within the structure. In general, the wand or receiver circuitry can be integrated into orthopedic equipment, devices, tools, and prosthetic components thereby eliminating the need to attach a wand or receiver to a component during a procedure. This allows the position and alignment of the integrated device to be tracked and also track relative to the muscular-skeletal system or other components. Referring briefly to FIGS. 2A and 2B, the wand or receiver electronics can be housed in prosthetic component 500. In particular, the disclosed electronics can be in one or both of modules 508. As a further example, the wand or receiver electronics can similarly be housed in a cutting block that is used in bone preparation to receive a prosthetic component as shown in FIG. 3A.

Prosthetic component 500 as illustrated is a knee insert for a total knee joint replacement. Prosthetic insert 500 can also be housed within a prosthetic component for the hip, spine, ankle, shoulder, and other muscular-skeletal joint or bone component. Prosthetic component 500 has articular surfaces 506 that support movement with the condyles of the femur and a load bearing surface 504 for distributing load to the tibia. Prosthetic component 500 can be an intra-operative device for providing quantitative measurement data on insert fit over the range of motion of the leg. Alternatively prosthetic component 500 can be a long-term implantable device. In one embodiment, prosthetic component 500 can include force, pressure, or load sensors for measuring load applied to articular surfaces 506. Quantitative measurement of joint loading in a trial phase of the procedure work flow supports assessment of the fit of prosthetic component 500 to determine selection of a final insert size.

Prosthetic component 500 comprises electronic modules 508, and transducers 510, 512, and 514. At least one electronic module 508 is operatively coupled to transducers 510, 512, and 514. In a first embodiment, electronic modules 508 can include circuitry as disclosed in FIG. 2A for transmitting ultrasonic signals. In a second embodiment, electronic modules 508 can include circuitry as disclosed in FIG. 2B for receiving ultrasonic signals. In a third embodiment electronic modules 508 can include both receiving and transmitting circuitry. Transducers 510, 512, and 514 are spaced apart at predetermined locations on prosthetic component 500 that approximate the spacing on a wand or receiver. The transducers are exposed to the external environment for sending or receiving ultrasonic signals. Transducers 510, 512, 514 are placed to be line of sight for transmitting or receiving an ultrasonic signal with at least one other navigation component when inserted in the muscular-skeletal system. The electronic circuitry is enclosed within prosthetic component 500 and isolated from an external environment. Although two modules are disclosed, prosthetic component 500 can include a single module or multiple modules.

The example uses the two modules to also provide load sensing capability. Modules 508 can include load sensing circuitry and force, pressure, or load sensors. The sensors can comprise mechanical, polymer, strain gauge, piezo-resistive, and other types of pressure sensors. Each module underlies an articular surface corresponding to a compartment of the knee. Sensors in each module measure a load applied to the corresponding articular surface. Modules 508 can include one or more sensors coupled to articular surfaces 506 for measuring load. In one embodiment, multiple sensors are used for each compartment to measure location of applied load on the articular surface.

In the example, load bearing surface 504 of prosthetic component 500 couples to a tibal prosthetic component. The tibial prosthetic component couples to a proximal end of the tibia. The tibial prosthetic component typically has one or more features for coupling to load bearing surface 504 and retaining prosthetic component 500. Thus, the tibial prosthetic component maintains a fixed relationship to prosthetic component 500 and the tibia.

One or more prosthetic components are typically coupled to a distal end of the femur. In the example, a femoral prosthetic component having condylar surfaces is coupled to the femur. The condylar surfaces are curved surfaces that couple to articular surfaces 506. Prosthetic component 500 when inserted between the tibial prosthetic component and the femoral prosthetic component forms a knee joint. The ligaments, tendons, and muscle around the prosthetic components hold the joint together under elastic tension throughout the range of motion. Transducers 510, 512, and 514 can transmit or receive ultrasonic signals with prosthetic component 500 in the joint. The condyle surfaces of the femoral prosthetic component can be motivated by the leg muscle to rotate on articular surfaces 506 of prosthetic component 500. The motion can be complex having both linear and rotational components.

In one embodiment, transmitter circuitry corresponding to a wand resides within prosthetic component 500. Transducers 510, 512, and 514 transmit ultrasonic signals to a receiver for reporting a location of prosthetic component 500 through time of flight and differential time of flight measurements. Load sensors in modules 508 can also provide quantitative load measurement data as the position and alignment is reported. Measurements can be in real-time and provide quantitative data at different locations in the range of motion. Thus, the location and alignment of prosthetic component 500 can be reported during the procedure when inserted into the joint without external componentry thereby providing maximum access to and around the muscular-skeletal system.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Other examples of positional measurement and alignment for orthopedic applications are herein contemplated. As another example a system and method for positioning and inserting a hip cup is provided. The Wand tip can register three locations on the hip to identify a docking target for a hip cup. The Wand 301 can then be affixed to a cup insert instrument to track its orientation relative to the registered docking target. A third example is a system and method for visualizing and reporting vertebral alignment in spine applications. The wand tip can register multiple location on the sacrum to identify a base coordinate system. The wand can then be affixed (or touched) to a vertebra to report alignment relative to the sacrum. The Wand can also be used to trace and report a spine contour for before and after comparison.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Where applicable, the present embodiments of the invention can be realized in hardware, software or a combination of hardware and software. Any kind of computer system or other apparatus adapted for carrying out the methods described herein are suitable. A typical combination of hardware and software can be a mobile communications device with a computer program that, when being loaded and executed, can control the mobile communications device such that it carries out the methods described herein. Portions of the present method and system may also be embedded in a computer program product, which comprises all the features enabling the implementation of the methods described herein and which when loaded in a computer system, is able to carry out these methods.

While the preferred embodiments of the invention have been illustrated and described, it will be clear that the embodiments of the invention are not so limited. Numerous modifications, changes, variations, substitutions and equivalents will occur to those skilled in the art without departing from the spirit and scope of the present embodiments of the invention as defined by the appended claims.

What is claimed is:

1. A system for positional measurements, comprising:
three or more ultrasonic transmitters on a first device for transmitting at a first location a first sequence of ultrasonic signals through air;
three or more receivers on a second device for capturing the first sequence of ultrasonic signals and a second sequence of ultrasonic signals transmitted by the ultrasonic transmitters on the first device during movement to a second location;
an orthopedic device coupled to the first device;
a phase detector on the second device operatively coupled to the receiver for identifying a series of phase differences between the first sequence of ultrasonic signals and the second sequence of ultrasonic signals; and
a processor on the second device operatively coupled to the phase detector and a sensing unit comprising the receiver for updating an expected location of the first device using the series of phase differences, wherein the processor:
measures a first series of Time of Flights (TOF) between the transmitting of the first sequence of ultrasonic signals and the capturing of the second sequence of ultrasonic signals, and producing therefrom the expected location of the first device at the first location,
measures a second series of Time of Flights (TOF) between the transmitting of the first sequence of ultrasonic signals and the capturing of the second sequence of ultrasonic signals, and producing therefrom an estimated location of the first device at the second location,
determines a relative displacement of the first device by weighting a difference of the expected location and estimated location with the phase difference, and
reports a position of an orthopedic device coupled to the first device in accordance with the relative displacement, wherein the estimated location is determined from the second series of Time of Flight (TOF) measurements, and the relative displacement is evaluated within a minimized error region determined from a series of differential time of flight (dTOF) measurements.

2. The system of claim 1, further comprising a third device to transmit ultrasonic signals to the second device for reporting a position and orientation of the third device relative to the second device, where the second device is attached to a first bone and the third device is attached to a second bone for communicating there between during range of motion.

3. The system of claim 1, wherein the second device synchronizes transmit operation of the first device and the third device by staggering transmit pulse time intervals.

4. The method of claim 1, where the processor:
saves to memory three or more anatomical location points on each of the first bone and the second bone identified by the first device at different times; and
reports an alignment of the three or more points on each of the first bone and the second bone of the first device at different times wherein the processor applies a weighted average to a history of estimated locations for determining the expected location.

5. The system of claim 1, wherein the processor reports an orientation of the orthopedic device attached to the first device at the position.

6. The system of claim 1, wherein the processor modifies a timing sequence of the ultrasonic signals transmitted from the first device based on a detected acceleration of the first device.

7. The system of claim 1, wherein the orthopedic device is a cutting jig.

8. The system of claim 2, wherein the orthopedic device is a prosthetic component.

9. The system of claim 2, wherein the orthopedic device is a trial insert.

10. A system for positional measurements, comprising:
three or more ultrasonic transmitters on a first device for transmitting at a first location a first sequence of ultrasonic signals through air, and three or more receivers on a second device for receiving the first sequence of ultrasonic signals and thereafter receiving a second sequence of ultrasonic signals transmitted by the first device;

a phase detector on the second device operatively coupled to the receivers for identifying a series of phase differences between the first sequence of ultrasonic signals and the second sequence of ultrasonic signals; and a processor operatively coupled to the phase detector and the sensing unit to:
measure a first series of Time of Flights (TOF) for the first sequence of received ultrasonic signals to produce an expected location of the object at a first location,
measure a second series of Time of Flights (TOF) for the second sequence of received ultrasonic signals to produce an estimated location of the object at a second location,
apply a weighted difference of the expected location and the estimated location to the phase difference to produce a relative displacement,
update the expected location of the first device with the relative displacement, and
report the expected location of a cutting jig coupled to the first device.

11. The system of claim 10, wherein the processor identifies the estimated location of the first device, and determines if the estimated location is within a region of relative displacement error of the expected location determined from differential time of flight (dTOF) measurements in view of the phase difference.

12. The input device of claim 10, wherein the processor determines the relative displacement of the object in view of the phase difference, the estimated location, and the expected location.

13. The input device of claim 10, wherein the processor saves to memory three or more location points of the first device at different times; and reports an alignment of the three or more points of the first device at different times.

14. The input device of claim 10, wherein the processor reports an orientation of the first device at the expected location.

15. A method resolving object movement and position, the method comprising the steps of:
receiving a first set of ultrasonic signals transmitted from a first device, where the first set of ultrasonic signals are measured by a transducer, where the first set of ultrasonic signals are used by a processor to calculate a first sequence of Time of Flight (TOF) measurements, where the first sequence of Time of Flight measurements is stored as a first data set in computer readable memory;
monitoring a movement of the first device from the first sequence of Time of Flight (TOF) measurement, where the first sequence of Time of Flight measurements is used by the processor to calculate an expected location of the first device;
receiving a second set of ultrasonic signals transmitted from the first device, where the second set of ultrasonic signals are measured by the transducer, where the second set of ultrasonic signals are used by the processor to calculate a second sequence of Time of Flight (TOF) measurements, where the second sequence of Time of Flight measurements is stored as a second data set in the computer readable memory;
estimating a second location of the first device, where the processor uses the second data set to calculate the estimated location of the first device;
calculating a set of phase differences between the first sequence of Time of Flight (TOF) measurements and the second sequence of Time of Flight (TOF) measurements, where the set of phase differences are calculated by the processor using the first and second data sets;
weighting a difference of the expected location and estimated location with the set of phase differences to produce a relative displacement of the first device, where the relative displacement is stored as a third data set in computer readable memory;
updating the expected location of the first device, where the processor uses the relative displacement and the estimated location to update the expected location and stores the updated expected location as a fourth data set in computer readable memory; and
reporting a position of a cutting jig coupled to the first device at the updated expected location.

16. The method of claim 15, further comprising:
determining if the estimated location is within a region of the relative displacement of the expected location in view of the set of phase differences; and
, if so, updating the expected location with a weighted difference of the estimated location and the relative displacement;
if not, updating the expected location with the relative displacement.

17. The method of claim 15 comprising:
saving to memory three or more location points of the first device at different times; and
reporting an alignment of the three or more points of the first device at different times.

18. The method of claim 15, comprising transmitting a plurality of ultrasonic signals from the first device at staggered time intervals to produce at least one of the first and second sequences.

19. The method of claim 15, comprising transmitting a plurality of ultrasonic signals from the first device at a same time to produce at least one of the first and second sequences.

20. The method of claim 15, further comprising performing a time weighted average of expected locations for updating the relative displacement.

21. The method of claim 20, further comprising modifying a timing sequence of the ultrasonic signals transmitted from the first device based on a detected acceleration of the first device.

22. A system for positional measurements, comprising:
three ultrasonic transmitter on a first device for transmitting at a first location a first sequence of ultrasonic signals through air;
a receiver on a second device for capturing the first sequence of ultrasonic signals and a second sequence of ultrasonic signals transmitted by the ultrasonic transmitter on the first device during movement to a second location;
a cutting jig coupled to the first device;
a phase detector on the second device operatively coupled to the receiver for identifying a series of phase differences between the first sequence of ultrasonic signals and the second sequence of ultrasonic signals; and
a processor on the second device operatively coupled to the phase detector and a sensing unit comprising the receiver for updating an expected location of the first device using the series of phase differences for:
measuring a first series of Time of Flights (TOF) between the transmitting of the first sequence of ultrasonic signals and the capturing of the second sequence of ultrasonic signals, and producing therefrom the expected location of the first device at the first location, measuring a second series of Time of Flights (TOF) between the transmitting of the first sequence of ultrasonic signals and the capturing of the second sequence of ultrasonic signals, and producing therefrom an estimated location of the first device at the second location, determining a relative displacement of the first device by weighting a difference of the expected location and estimated location with the phase difference, and reporting a position of a cutting jig coupled to the first device in accordance with the relative displacement wherein the estimated location is determined from the second series of Time of Flight (TOF) measurements, and the relative displacement is evaluated within a minimized error region determined from a series of differential time of flight (dTOF) measurements.

23. The system of claim 22, further comprising a third device for transmitting ultrasonic signals to the second device for reporting a position and orientation of the third device relative to the second device, where the second device is attached to a first bone and the third device is attached to a second bone for communicating there between during range of motion wherein the second device synchronizes transmit operation of the first device and the third device by staggering transmit pulse time intervals.

24. The method of claim 22, where the processor:
saves to memory three or more anatomical location points on each of the first bone and the second bone identified by the first device at different times; and
reports an alignment of the three or more points on each of the first bone and the second bone of the first device at different times wherein the processor applies a weighted average to a history of estimated locations for determining the expected location.

25. The system of claim 22, wherein the processor reports an orientation of the cutting jig coupled to the first device at the position.

26. The system of claim 22, where the first device is housed within the cutting jig.

27. A system for positional measurements, comprising:
an ultrasonic transmitter on a first device for transmitting at a first location a first sequence of ultrasonic signals through air;
a receiver on a second device for capturing the first sequence of ultrasonic signals and a second sequence of ultrasonic signals transmitted by the ultrasonic transmitter on the first device during movement to a second location;
a prosthetic insert coupled to the first device;
a phase detector on the second device operatively coupled to the receiver for identifying a series of phase differences between the first sequence of ultrasonic signals and the second sequence of ultrasonic signals; and
a processor on the second device operatively coupled to the phase detector and a sensing unit comprising the receiver for updating an expected location of the first device using the series of phase differences for:
measuring a first series of Time of Flights (TOF) between the transmitting of the first sequence of ultrasonic signals and the capturing of the second sequence of ultrasonic signals, and producing therefrom the expected location of the first device at the first location,
measuring a second series of Time of Flights (TOF) between the transmitting of the first sequence of ultrasonic signals and the capturing of the second sequence of ultrasonic signals, and producing therefrom an estimated location of the first device at the second location,
determining a relative displacement of the first device by weighting a difference of the expected location and estimated location with the phase difference, and
reporting a position of a prosthetic insert having at least one articular surface coupled to the first device in accordance with the relative displacement wherein the estimated location is determined from the second series of Time of Flight (TOF) measurements, and the relative displacement is evaluated within a minimized error region determined from a series of differential time of flight (dTOF) measurements.

28. The system of claim 27, further comprising a third device for transmitting ultrasonic signals to the second device for reporting a position and orientation of the third device relative to the second device, where the second device is attached to a first bone and the third device is attached to a second bone for communicating there between during range of motion wherein the second device synchronizes transmit operation of the first device and the third device by staggering transmit pulse time intervals.

29. The method of claim 28, where the processor:
saves to memory three or more anatomical location points on each of the first bone and the second bone identified by the first device at different times; and
reports an alignment of the three or more points on each of the first bone and the second bone of the first device at different times wherein the processor applies a weighted average to a history of estimated locations for determining the expected location.

30. The system of claim 27, wherein the processor reports an orientation of the prosthetic insert coupled to the first device at the position.

* * * * *